(12) United States Patent
Sawai et al.

(10) Patent No.: US 7,610,154 B2
(45) Date of Patent: Oct. 27, 2009

(54) METHOD AND APPARATUS FOR CHEMICAL GENETIC PROGRAMMING

(75) Inventors: Hidefumi Sawai, Koganei (JP); Hideaki Suzuki, Kyoto (JP); Wojciech Piaseczny, Kyoto (JP)

(73) Assignees: National Institute of Information and Communications Technology, Tokyo (JP); Advanced Telecommunications Research Institute International, Kyoto (JP)

( * ) Notice: Subject to any disclaimer, the term of this patent is extended or adjusted under 35 U.S.C. 154(b) by 487 days.

(21) Appl. No.: 11/050,816

(22) Filed: Jan. 27, 2005

(65) Prior Publication Data

US 2005/0192762 A1 Sep. 1, 2005

(30) Foreign Application Priority Data

Jan. 27, 2004 (JP) ............................. 2004-018802

(51) Int. Cl.
*G06F 19/00* (2006.01)
*G06N 3/00* (2006.01)
(52) U.S. Cl. ........................................ 702/19; 706/13
(58) Field of Classification Search ........................ None
See application file for complete search history.

(56) References Cited

U.S. PATENT DOCUMENTS 7,024,312 B1 * 4/2006 Selifonov et al. ............. 702/19

2001/0039014 A1 * 11/2001 Bass et al. ..................... 435/6
2002/0102734 A1 * 8/2002 Menzel ....................... 435/475

OTHER PUBLICATIONS

Suzuki et al.; "Chemical Genetic Algorithms —Coevolution Between Codes and Code Translation"; *Proceedings of the Eighth International Conference on Artificial Life*; Artificial Life VIII; c. 2002; pp. 164-172.
Suzuki et al.; "Evolvability Enhancement by the Optimization of a Chemical Translation System —a Case Study"; *The 7th European Conference on Artificial Life (ECAL) Workshop Proceeding*: c. 2003; pp. 146-155.
John R. Koza; Genetic Programming: On the Programming of Computers by Means of Natural Selection; *The MIT Press*; c. 1992; pp. 79-119.

* cited by examiner

*Primary Examiner*—Lori A Clow
(74) *Attorney, Agent, or Firm*—McDermott Will & Emery LLP

(57) ABSTRACT

A chemical genetic programming apparatus is provided, which enables programming by the application of a chemical genetic algorithm. A CPU 120 includes a tRNA transcripting unit 1201 performing transcription of tRNA from a second portion of DNA, an amino acid translating unit 1202 translating amino acids based on a third portion of DNA and an aminoacyl-tRNA table, an aminoacyl-tRNA updating unit 1203 updating the aminoacyl-tRNA table by a reaction of amino acids and tRNAs, and a phenotype tree generating unit 1205 for generating a phenotype tree by translation based on the aminoacyl-tRNA table and the first portion of DNA, and performs genetic operations on the DNA.

2 Claims, 12 Drawing Sheets

FIG.8

| I | N | R | Z | O | D |
|---|---|---|---|---|---|
| I→N | N→(NON)<br>N→R<br>N→Z | R→x<br>R→Z<br>R→ZZ<br>R→N^N | Z→D<br>Z→ZZ | O→+<br>O→−<br>O→*<br>O→/ | D→0<br>D→1<br>D→2<br>D→3<br>D→4<br>D→5<br>D→6<br>D→7<br>D→8<br>D→9 |

METHOD AND APPARATUS FOR CHEMICAL GENETIC PROGRAMMING

BACKGROUND OF THE INVENTION

1. Field of the Invention

The present invention relates to an apparatus for chemical genetic programming and a method of chemical genetic programming.

2. Description of the Background Art

In biological cells, translation from symbol to function, that is, translation from genotype to phenotype is specified by enzymes created from DNA (DeoxyriboNucleic Acid), and therefore, when cells are subjected to gene modification, translation process is also influenced by the modification. DNA is translated into transfer RNAs (tRNA: transfer Ribo-Nucleic Acid). The translated tRNAs react with amino acids by the help of enzyme to generate a translation table, that is, aminoacyl-tRNAs, specifying the translation scheme of the cell. Information related to code structure specifying the genotype and information or code translation are both stored in DNA, and therefore, both can coevolve in the cells through gene mutation.

(Chemical Genetic Algorithm)

A new genetic algorithm, referred to Chemical Genetic Algorithm (CGA) has been proposed, through inspiration to mimic the mechanism in the actual biological cells (see, for example, Reference 1: Suzuki, H., Sawai, H.: "Chemical Genetic Algorithms—Coevolution between Codes and Code Translation." In: Standish, R. K., Bedau, M. A., Abass, H. A. (eds.): Proceedings of the Eighth International Conference on Artificial Life (Artificial Life VIII) (2002) pp. 164-172, and Reference 2: Suzuki, H., Sawai, H., Piaseczny, W.: "Evolvability Enhancement by the Optimization of a Chemical Translation System—a Case Study." In: Dittrich, P., Kim, J. T. (eds.): The 7th European Conference on Artificial Life (ECAL) Workshop Proceedings (2003) pp. 146-155).

CGA introduces dynamic relation between the genotype information and the phenotype function, to enable autonomous optimization of the translation process from genotype to phenotype.

In a typical genetic algorithm, "encoding" for defining correspondence or mapping between DNA in binary representation and a function parameter to be optimized is the most important factor that determines the performance of the algorithm. The determining relation is, in "chemical genetic algorithm," autonomously established.

Such an algorithm may be used as an optimization algorithm. Optimization is one of the most required processes in various and many fields of technology. Chemical genetic algorithm is an approach for building an intelligent system similar to biological system.

An ability to evolve in an artificially designed evolutionary system is specified by a set of fundamental functional units. In a real biological system, the fundamental functional units include twenty amino acids, and genetic information written in DNA is translated into these amino acids by using a set of molecules known as "aminoacyl-tRNAs". In the biological system, aminoacyl-tRNAs are fundamental molecules defining mapping from genotype (genetic type; base sequence on DNA, genetic code) to phenotype (protein functions and the like).

The process for selecting amino acids as functional units in real biological system and selecting aminoacyl-tRNAs as translation molecules thereto takes place simultaneously with evolution of genotype (codes) written in DNA/RNA, and in this sense, the codes and the translation table therefor "evolved simultaneously," or in a broad sense, "coevolved".

In an artificial evolutionary system, the introduction of coevolution between codes and translation table might help spontaneous enhancement of evolutionary performance during evolutionary experiments.

"Chemical genetic algorithm" represents a method developed from the genetic algorithm based on analogy to bio-metabolic system.

In typical genetic algorithm, first, a population of chromosomes are prepared and subjected to genetic operations such as mutation and crossover. In contrast, in "chemical genetic algorithm" (hereinafter referred to as CGA), not a population of chromosomes but cells are prepared.

A cell not only includes a common chromosome (DNA) but also three small molecular groups of amino acids, tRNAs and aminoacyl-tRNAs, genetic codes on DNA are converted to real values through transcription and translation reactions in the cell, and fitness is computed.

Genetic operations include common DNA mutation, DNA crossover as well as molecular reaction and cytoplasmic exchange, and natural selection takes place by the unit of a cell containing the molecular groups.

(Genetic Programming)

Genetic programming, on the other hand, has found various technical applications (see, for example, Reference 3: Koza, J. R.: Genetic Programnming: On the Programming of Computers by Means of Natural Selection, The MIT Press (1992) pp. 79-119).

The conventional genetic programming starts from a program consisting of randomly generated prescribed programming elements, and reproduces over generations a best fit program of each generation through genetic operations, so as to evolve the population.

Though an approach to optimize functional parameter has been considered in CGA such as described above, it has been unclear how such approach should be applied to programming.

SUMMARY OF THE INVENTION

An object of the present invention is to provide an apparatus for chemical genetic programming and a method of chemical genetic programming, by using a chemical genetic algorithm to enable programming.

According to an aspect, the present invention provides a chemical genetic programming apparatus, including: storing means for storing genetic information of each individual, transfer information including a plurality of rule number-symbol pairs, rewriting information including mapping for rewriting the symbols, and a translation table obtained by combining the transfer information and the rewriting information; wherein the genetic information includes first information including a sequence of the rule numbers for generating a phenotype entity, second information for generating the transfer information, and third information including a sequence of the rule numbers for generating the rewriting information; the apparatus further including: transcripting means for generating the transfer information by transcription from the second information; first translating means for generating the rewriting information by translation based on the third information and the translation table; updating means for updating the translation table by combining the rewriting information and the transfer information; phenotype entity generating means for generating the phenotype entity by translation based on the first information and the translation table; selecting means for selecting among the individuals in accordance with fitness of a result represented by the phenotype entity with respect to a prescribed target; and mutating means for performing mutation on the genetic information.

Preferably, the chemical genetic programming apparatus further includes crossover processing means for performing crossover process on the genetic information, the transfer information and the rewriting information.

Preferably, the symbol includes a terminal symbol forming the result represented by the phenotype entity and indicating an end of translation, and non-terminal symbol indicating possibility of continuous translation; and the rewriting information includes continuous rewriting information from one of the non-terminal symbols to at least another one of the non-terminal symbols, and terminal rewriting information from one of the non-terminal symbols to one of the terminal symbols.

Preferably, the chemical genetic programming apparatus further includes exchanging means for exchanging among the individuals, the transfer information, the rewriting information, and information included in the translation table.

According to another aspect, the present invention provides a chemical genetic programming method for performing genetic programming based on genetic information including first information including a sequence of rule numbers for generating a phenotype entity, second information for generating transfer information having a plurality of rule number-symbol pairs, and third information including a sequence of the rule numbers for generating rewriting information having a mapping for rewriting the symbols, including: the first step of storing, in a storage area of a storage apparatus, the genetic information of each individual of current generation, the rewriting information, the transfer information and a translation table obtained by combining the transfer information and the rewriting information; the second step of generating the transfer information by transcription from the second information of the current generation and storing in the storage apparatus; the third step of generating the rewriting information by translation based on the third information and the translation table and storing in the storage apparatus; the fourth step of updating the translation table by combining the rewriting information and the transfer information; the fifth step of generating the phenotype entity by translation based on the first information and the translation table; the sixth step of selecting among the individuals in accordance with fitness of a result represented by the phenotype entity with respect to a prescribed target; the seventh step of updating generation of the genetic information by performing mutation on the genetic information and performing crossover operation of the genetic information; and repeating the first to seventh steps for a prescribed number of times.

By the chemical genetic programming apparatus and chemical genetic programming method of the present invention, a translation table of genetic information is prepared, and a feedback mechanism is provided in which rewriting information and transfer information formed from the genetic information generate a new translation table, whereby "coevolution of codes and translation table" is realized, so that optimal result of programming can be obtained in a short time.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 shows examples of initially prepared amino acids.

DESCRIPTION OF THE PREFERRED EMBODIMENTS

Embodiments of the present invention will be described in the following with reference to the figures.

(System Configuration of the Present Invention)

Figure 1:
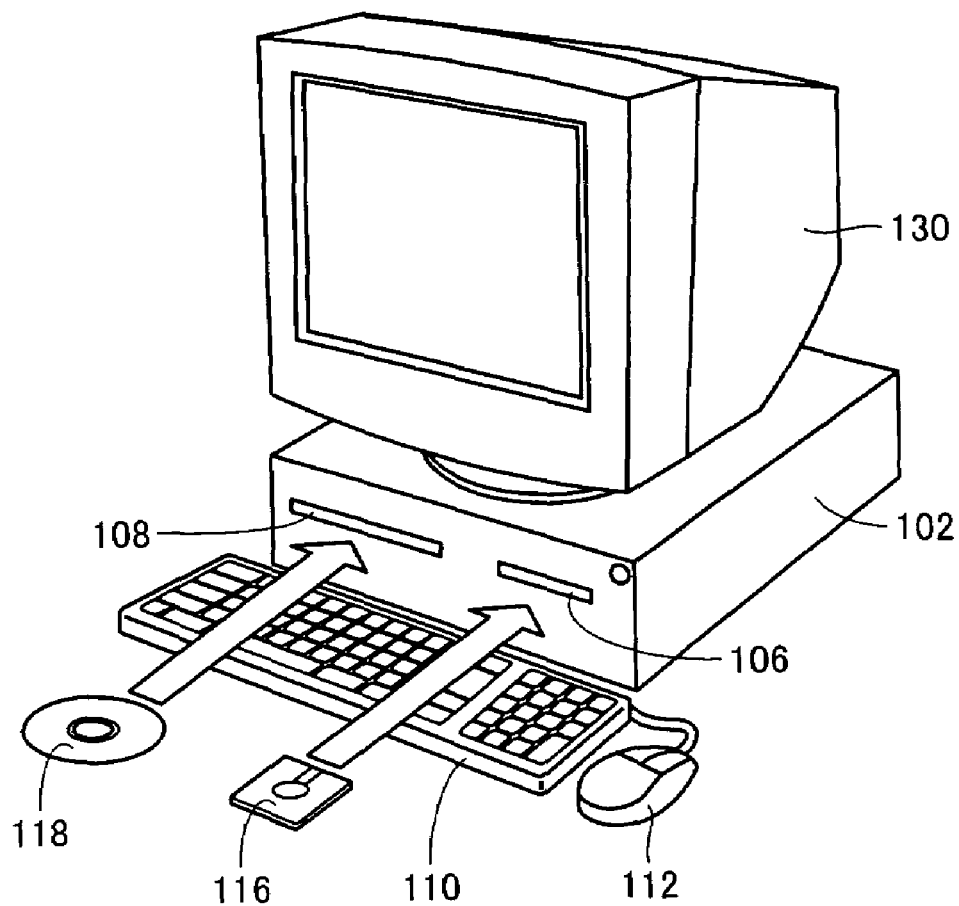
FIG. 1 shows an appearance of a chemical genetic programming apparatus 100 in accordance with the present invention.

FIG. 1 shows an appearance of a chemical genetic programming apparatus 100 in accordance with the present invention.

Specifically, in the example shown in FIG. 1, chemical genetic programming apparatus 100 is implemented by a general-purpose computer.

Referring to FIG. 1, chemical genetic programming apparatus (computer 100) includes a computer body 102 provided with a CD-ROM drive 108 for reading information on a CD-ROM (Compact Disc Read-Only Memory) and an FD drive 106 for reading and writing information to and from a flexible disk (hereinafter denoted by FD) 116, a display 130 as a display apparatus connected to computer body 102, and an input unit (a keyboard) 110 and a mouse 112 as input apparatuses also connected to computer body 102.

Figure 2:
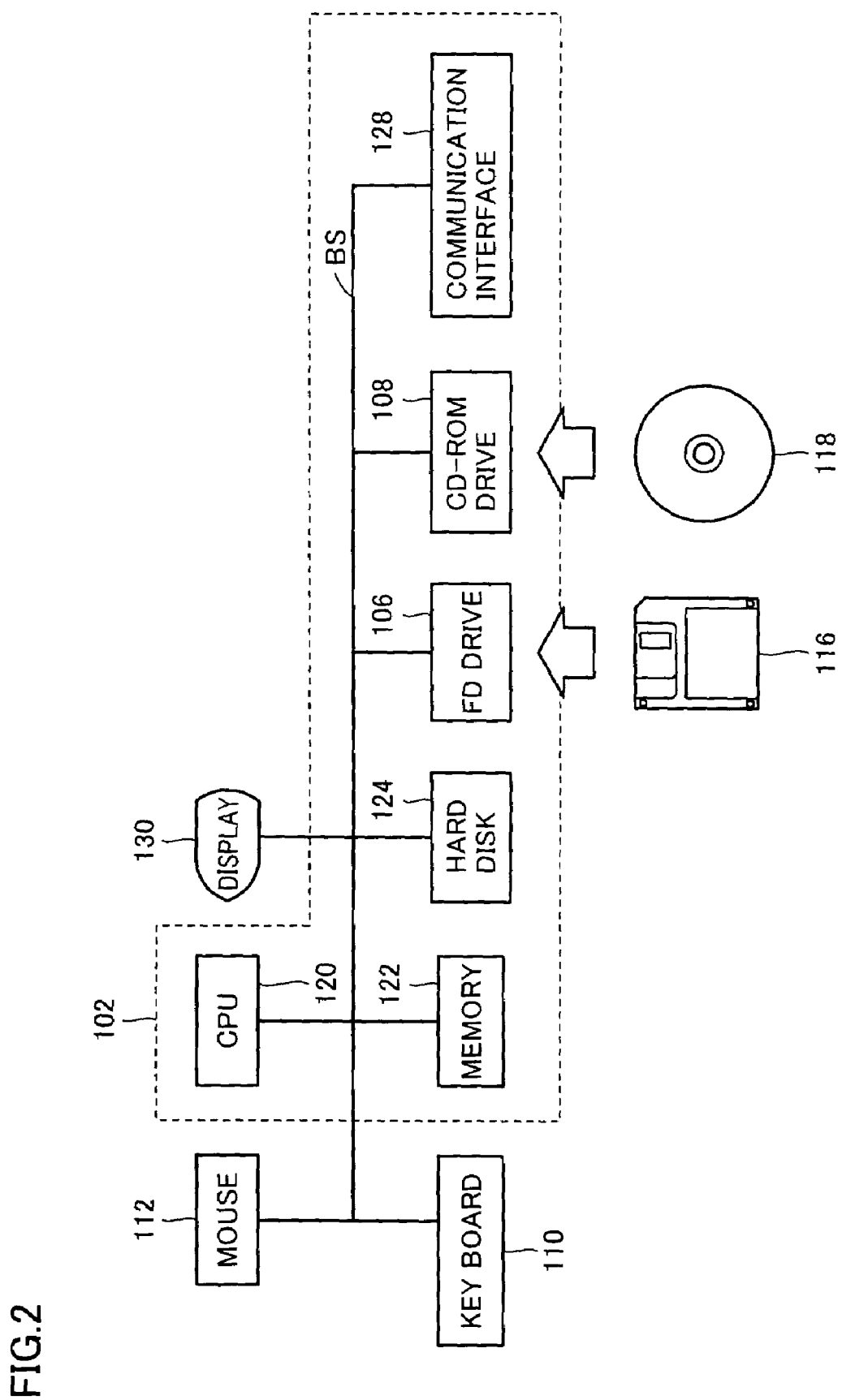
FIG. 2 is a block diagram representing a hardware configuration of chemical genetic programming apparatus 100.

FIG. 2 is a block diagram representing the hardware configuration of chemical genetic programming apparatus 100.

As shown in FIG. 2, computer body 102 as chemical genetic programming apparatus 100 includes, in addition to CD-ROM drive 108 and FD drive 106, a CPU (Central Processing Unit) 120, a memory 122 including an ROM (Read Only Memory) and an RAM (Random Access Memory), a direct access memory device such as a hard disk 124, and a communication interface 128 for exchanging data to and from a network 200, each connected to a bus BS. A CD-ROM 118 is mounted to CD-ROM drive 108, and an FD 116 is mounted to FD drive 106.

It is noted that CD-ROM 118 may be replaced by any other medium such as DVD-ROM (Digital Versatile Disc) or a memory card that can record information such as a program to be installed in the computer. In that case, computer body 102 has a drive that can read such media.

A main portion of the chemical genetic programming apparatus in accordance with the present invention is provided by computer hardware and software executed by CPU 120. Generally, such software is distributed stored in a storage medium such as CD-ROM 118 or FD 116, read by CD-ROM drive 108 or FD drive 106 from the storage medium and temporarily stored in hard disk 124. Alternatively, when the apparatus is connected to a network, the software may be temporarily copied from a network server to hard disk 124. Then, the software is read from hard disk 124 to RAM in memory 122, and executed by CPU 120. It is noted that when the apparatus is connected to a network, the software may not necessarily be stored in hard disk 124 and it may be directly loaded to the RAM for execution.

The hardware of the computer shown in FIGS. 1 and 2 and the principle of operation thereof are generally known. Therefore, the essential part of the present invention resides in the software stored in the storage medium such as FD 116, CD-ROM 118 or hard disk 124.

It is a general practice that various program modules are prepared as parts of an operating system of a computer, and an application program calls these modules in a prescribed order as needed for processing. In such a case, the software to realize chemical genetic programming apparatus 100 itself does not include these modules, and chemical genetic programming apparatus 100 is realized for the first time when it co-operates with the operating system of the computer. As long as a general platform is used, however, it is unnecessary to deliver the software including such modules. Therefore, the software itself without such modules and the recording medium recording the software (as well as data signals representing the software delivered through a network) is considered to be an embodiment of the invention.

(Transcription and Translation Mechanism in Biological System)

As a premise of the operation of chemical genetic programming apparatus in accordance with the present invention, metabolic system in a real biological cell will be briefly described.

Figure 3:
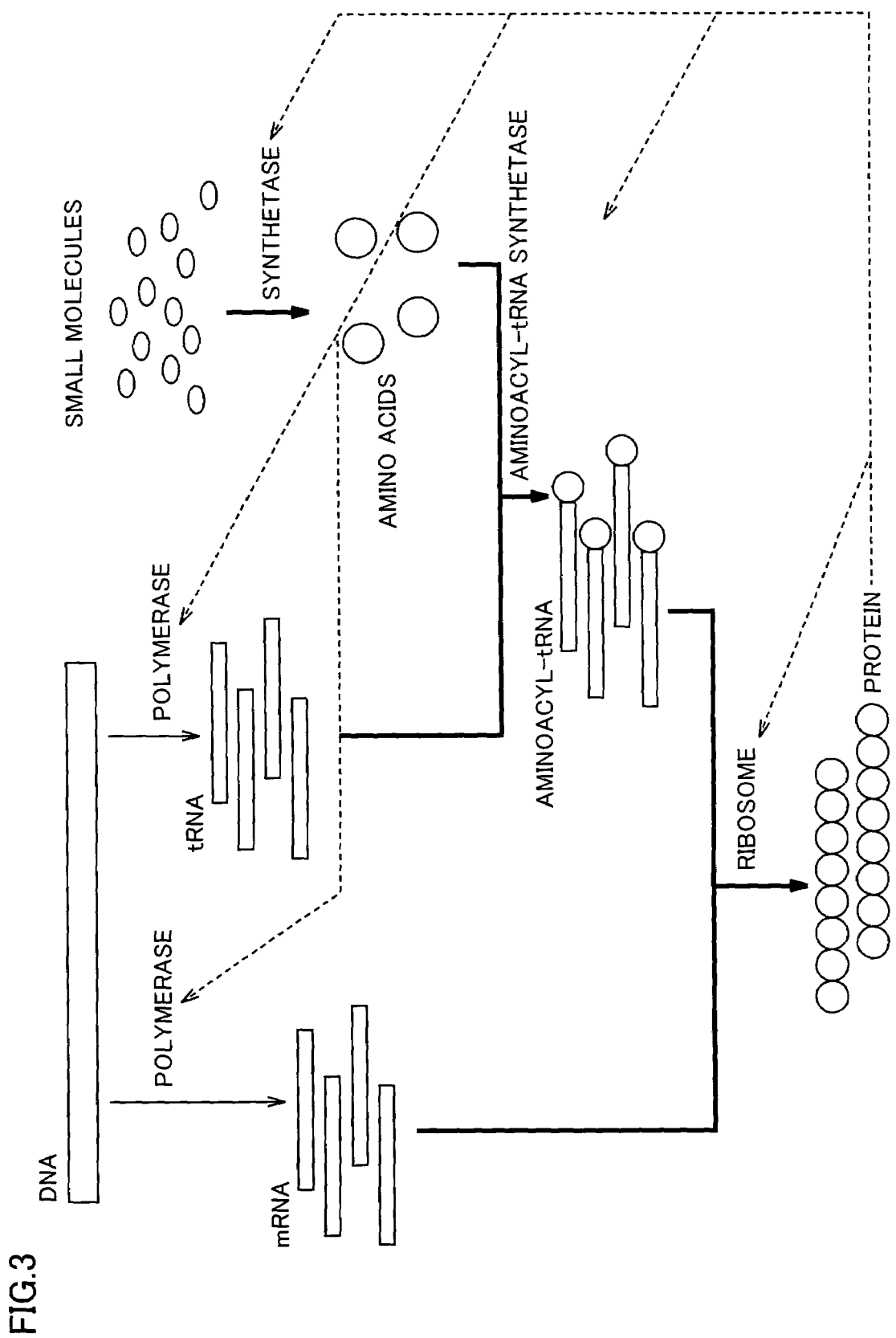
FIG. 3 is an illustration schematically showing metabolism in real biological cells.

FIG. 3 is a schematic illustration of the metabolic mechanism in a real biological cell.

Referring to FIG. 3, the translation of genetic information in a biological cell is achieved by metabolic reactions by a group of molecules. First, an organism prepares amino acids from inorganic material by biosynthesis. This is mainly attained by photosynthesis by plants, and amino acids are produced as by-products of a series of glycolysis operations starting from sugars produced by the photosynthesis. Animals obtain amino acids by taking and digesting amino acids produced by plants.

On the other hand, the genetic information of DNA proceeds along two main flows.

First, tRNAs formed by polymerase transcription of DNA are coupled with amino acids, resulting in aminoacyl-tRNAs. A tRNA is a sequence of about 80 polynucleotides, which is folded into a particular clover-shaped structure in the cell.

At one end of the structure, there is an anti-codon, which complementarily matches a codon in mRNA, and at the other end, there is an identifier portion, which matches an amino acid. Thus, tRNA having this particular structure functions as an adaptor between codon and amino acid.

The tRNA is coupled with an amino acid by means of a group of enzymes called aminoacyl-tRNA synthetase (ATS). An aminoacyl-tRNA synthetase sticks to the amino acid identifier portion of the clover-shaped structure of tRNA, finds a matching amino acid and combines them. It is known that for each amino acid, one specific aminoacyl-tRNA synthetase is prepared, and therefore, in a cell, twenty different aminoacyl-tRNA synthetases are used.

Another flow of the genetic information of DNA is translation of mRNA accomplished by polymerase transcription from DNA. The mRNA is an information high polymer holding codon sequence information, and serves as a base for amino acid sequence of protein. Ribosome, which is a giant protein structure, reads codons in mRNA one by one, finds aminoacyl-tRNAs having matching anti codons, and joins the amino acids coupled thereto into a chain. A polypeptide chain obtained in this manner again catalyzes, as an enzyme, various metabolic reactions of the cells.

The mechanism for translating biological genetic information described above is characterized by the changeability of mapping (translation table) between the genotype to the phenotype in the living organism. In life, aminoacyl-tRNA, which is a molecule having a codon (genotype unit) and an amino acid (phenotype unit) coupled directly, represents the translation table. The aminoacyl-tRNAs are created in reference to tRNA transcribed from DNA, and therefore, the translation table can be changed by modifying the DNA information.

Another important characteristic of the biological translation mechanism is that the metabolic map is not one-directional but has a feedback mechanism.

Specifically, all metabolic reactions in cells including translation are catalyzed by enzymes, which enzymes themselves are produced by metabolic reactions, so that molecules in cells are interdependent in a complex manner. As to the translation of genetic information in particular, the aminoacyl-tRNA synthetase as the enzyme synthesizing aminoacyl-tRNA is synthesized by ribosome through translation of codes encoding the aminoacyl-tRNA as protein. Consequently, the code (codon sequence representing aminoacyl-tRNA synthetase) and the translation table (aminoacyl-tRNA) depend on each other and coevolve.

(Outline of Chemical Genetic Programming)

In the following, the scheme of "chemical genetic programming" in accordance with the present invention modeled after the actual metabolic reactions in life will be briefly described.

(Intracellular Metabolism)

Figure 4:
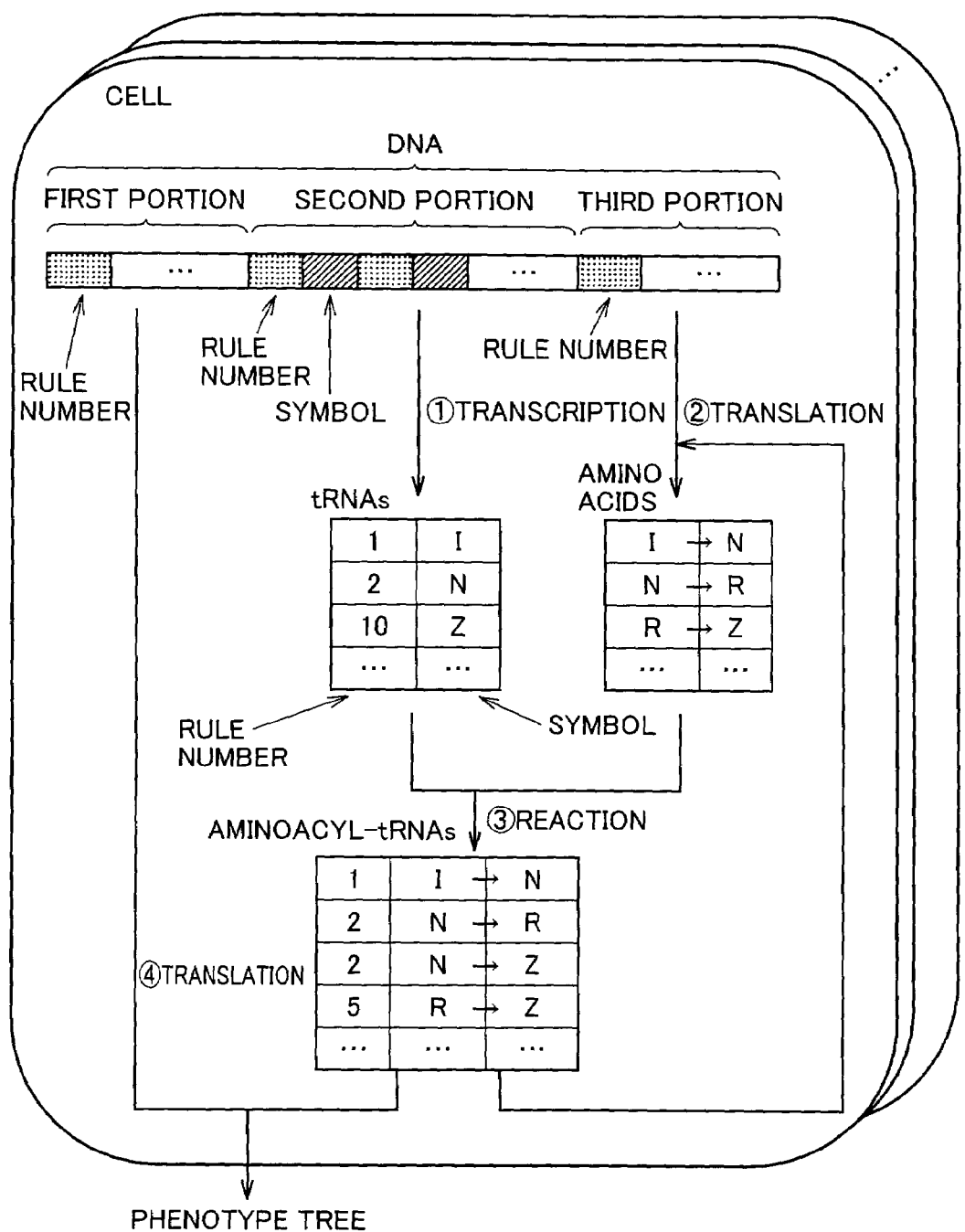
FIG. 4 is a schematic illustration of a basic flow of chemical genetic programming.

FIG. 4 is an illustration schematically representing a basic flow of the chemical genetic programming process.

Referring to FIG. 4, first, assume a plurality of artificial cells (individuals) each having the following four molecules. Namely, one DNA, $L_1$ tRNAs, $M_1$ amino acids, and $R_1$ aminoacyl-tRNAs.

These artificial molecules go through the following metabolic reaction every generation.

It is assumed that each DNA has first, second and third portions.

The first portion of DNA has information (rule number) for translating a "phenotype tree" created by the chemical genetic programming, as will be described later.

The second portion of DNA includes information for creating the t-RNA table by transcription. The second portion includes a plurality of rule number-symbol pairs. The pair of rule number and symbol is modeled after the actual biological tRNA, which has an anti codon complementarily matching mRNA at one end and an identifier portion matching amino acid at the other end. It is noted, however, that in the chemical genetic programming of the present invention, the component corresponding to mRNA is not included, as will be described later. Therefore, the rule number of the tRNA table will be in correspondence to the rule number of the first portion of DNA through an aminoacyl-tRNA table, which will be described later. Here, the same rule numbers correspond to each other.

Here, the "symbol" may be alphabets, numerical symbols, numbers and the like that form a phenotype tree. Any other marks or figures may be used as symbols, as needed. It is assumed that the symbols include a terminal symbol and a non-terminal symbol. If a certain function is to be generated at the end of programming, the final function may be represented by alphabets for variables (for example, x) and mathematical symbols (operation symbols: for example, + and −). Therefore, symbols included in the final form of such programming are terminal symbols, and other symbols are non-terminal symbols.

The third portion of DNA includes information for generating amino acids through translation.

Each "amino acid" corresponds to the symbol rewriting mapping described above. Here, the mapping for rewriting will be represented as "A→B", in which "A" will be referred to as a start symbol, and "B" as a rewrite symbol.

Here, "transcription" corresponds to a process of copying the DNA information as it is, and "translation" corresponds to a process of rewriting symbols corresponding to the DNA information (rule number) in accordance with the aminoacyl-tRNA table, which will be described later.

Specifically, starting from a prescribed non-terminal symbol, rewriting proceeds in accordance with the information of the first portion of DNA. Because of branches made in the process, the rewriting produces a tree structure. Such a tree is referred to as a "phenotype tree." When ends of all branches of the phenotype tree come to have terminal symbols, translation of the first portion of DNA ends. The result represented by the ends of branches of the thus generated phenotype tree at the end of translation will be referred to as a "phenotype entity."

Principal operation shown in FIG. 4 will be briefly described.

First, from L rule number-symbol pairs of the second portion of DNA, L tRNAs are created by transcription and added to the group of tRNA table. When the number of tRNAs exceeds $L_1$, tRNAs are randomly chosen and eliminated.

Thereafter, from M rule numbers of the third portion of DNA, M amino acids are formed by translation. Translation is performed using an existing group of aminoacyl-tRNAs (aminoacyl-tRNA table), and aminoacyl-tRNAs having rule numbers matching the rule numbers on the DNA are selected at random. Amino acids having these are added to the group of amino acids (amino acid table).

Here again, when the number of amino acids exceeds $M_1$, some amino acids are randomly chosen and eliminated.

Then, molecular reaction between tRNAs and amino acids take place. When a randomly selected tRNA symbol matches a start symbol of a randomly selected amino acid, these two are coupled to create one aminoacyl-tRNA. This operation is repeated, and when $R_2$ new aminoacyl-tRNAs have been added to the aminoacyl-tRNA group, some aminoacyl-tRNAs are randomly chosen and eliminated, so that the number of aminoacyl-tRNAs does not exceed $R_1$. Consequently, it follows that one same rule number may have different mappings (amino acids) for rewriting, as shown in FIG. 4.

Next, from the rule number of the first portion of DNA, a phenotype tree is created by translation using aminoacyl-tRNAs.

The result of programming represented by the final form of phenotype tree, such as a function, is compared against an externally prepared target function, to compute cell fitness. As will be described later, cells are selected based on the fitness. For genetic programming, the cell is further subjected to DNA mutation, and crossover and molecular exchange among cells, and the process for one generation ends.

It is naturally understood that the reaction above does not fully mimic the biological translation mechanism. DNA does not have complete information of mRNA, and therefore, the proteins serving as enzymes cannot be formed by this model. The simplified metabolic system, however, has a feedback mechanism that aminoacyl-tRNA has a genetic information translation table and molecules formed by translation generate new aminoacyl-tRNAs. Thus, this system realizes biological "coevolution of codes and translation table."

(Functional Configuration of Chemical Genetic Programming Apparatus)

Figure 5:
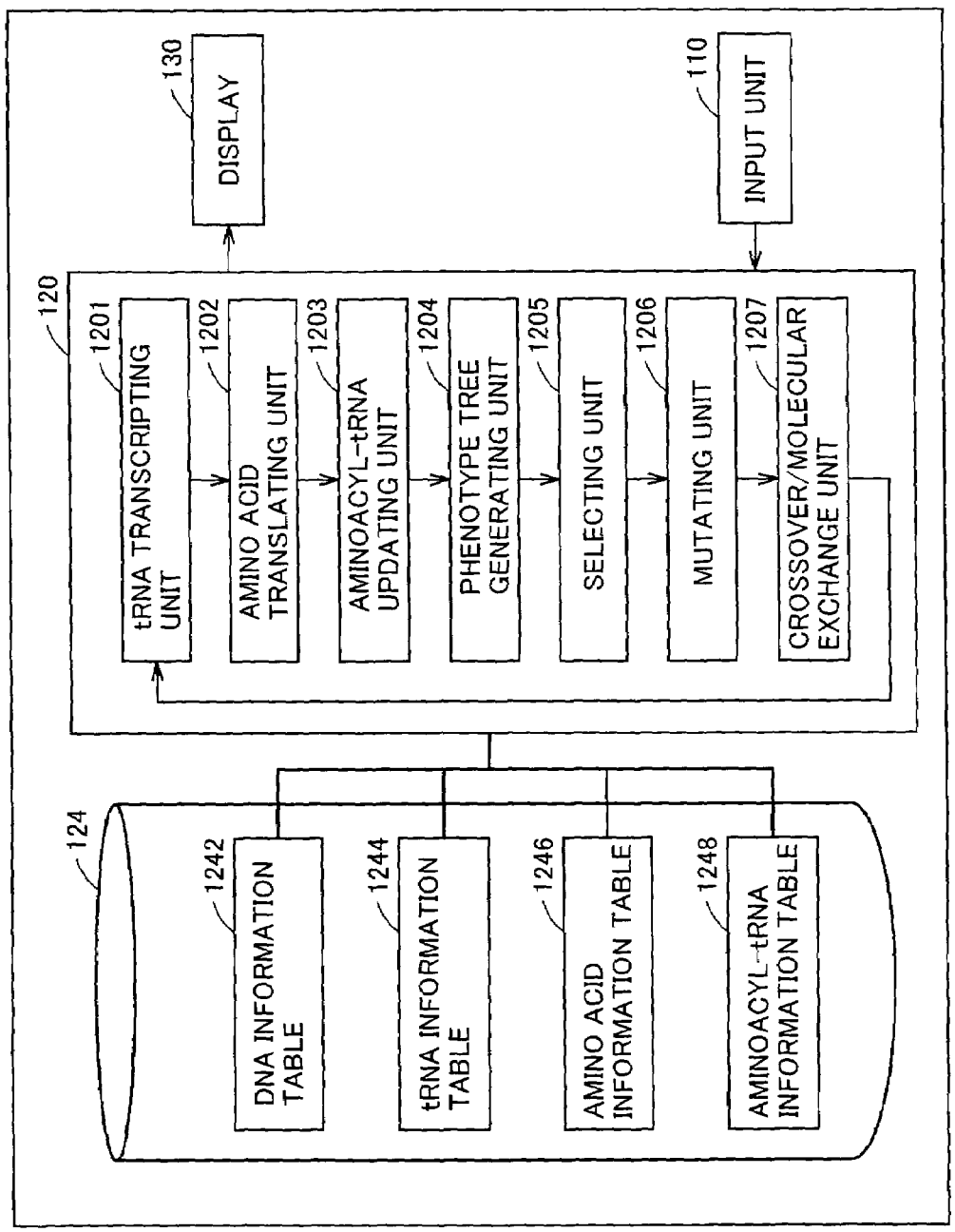
FIG. 5 is a functional block diagram of chemical genetic programming apparatus 100 shown in FIGS. 1 and 2.

FIG. 5 is a block diagram of chemical genetic programming apparatus described with reference to FIGS. 1 and 2.

In order to realize the process described with reference to FIG. 4, hard disk 124 stores a DNA information table 1242 for storing DNA information of each cell, a tRNA information table 1244 for storing a tRNA table generated by transcription in each cell, an amino acid information table 1246 for storing an amino acid table generated by translation in each cell, and an aminoacyl-tRNA information table 1248 for storing an aminoacyl-tRNA table generated by reaction in each cell.

CPU 120 performs processes based on programs stored in hard disk 124 and the like, and for such processes, the operating unit includes a tRNA transcripting unit 1201 for performing tRNA transcription from the second portion of DNA, an amino acid translating unit 1202 performing amino acid translation based on the third portion of DNA and the aminoacyl-tRNA table, an aminoacyl-tRNA updating unit 1203 for updating the aminoacyl-tRNA table by the reaction between amino acids and tRNAs, a phenotype tree generating unit 1204 for generating a phenotype tree by translation based on the aminoacyl-tRNA table and the first portion of DNA, a selecting unit 1205 for selecting cells based on fitness, a mutating unit 1206 for performing DNA mutation, and a crossover/molecular exchange unit 1207 for performing DNA crossover and molecular exchange operations.

(Genetic Operations)

In the following, specific processes of chemical genetic programming will be described.

Figure 6:
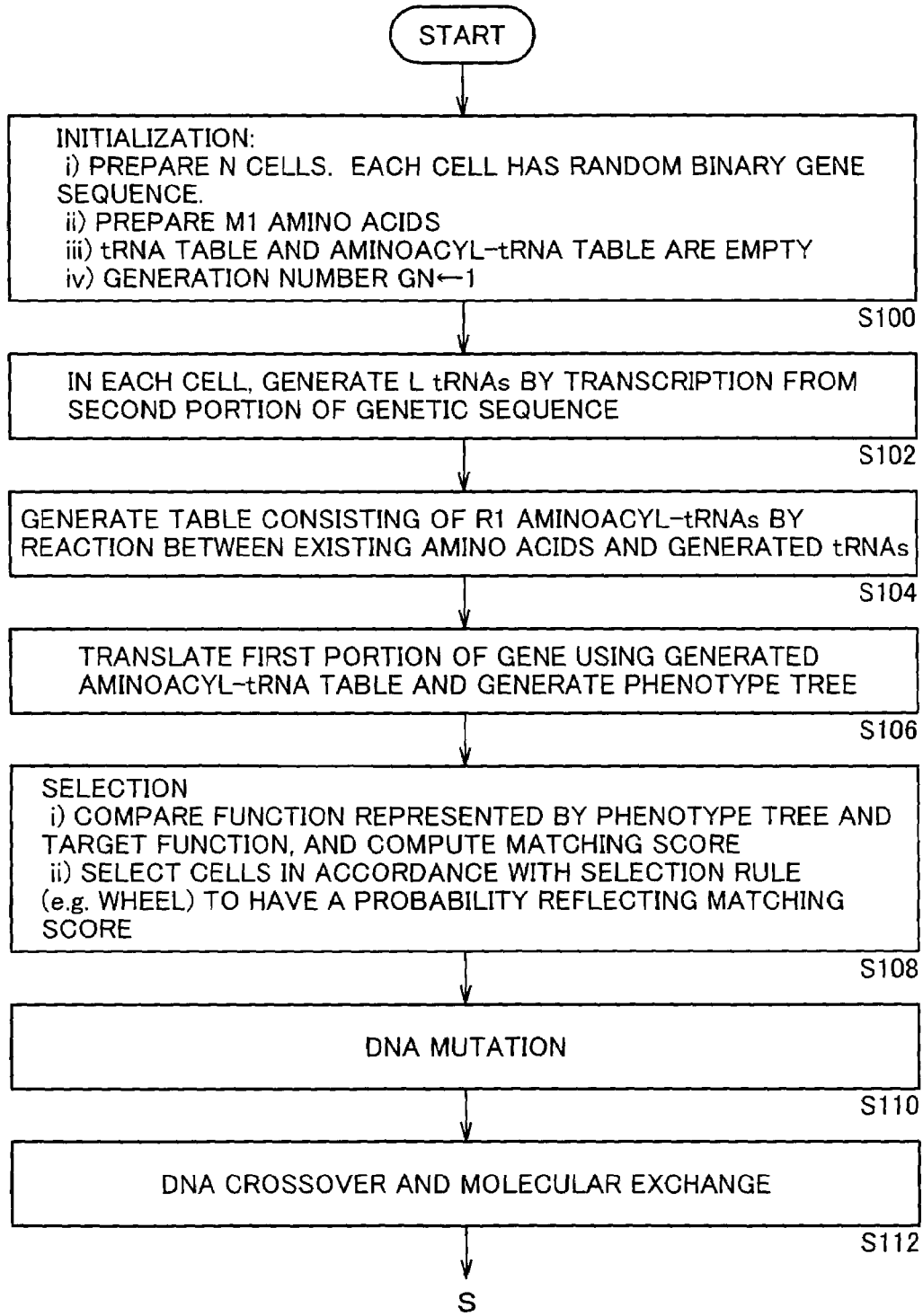
FIG. 6 is a first flow chart representing the flow of chemical genetic programming.
Figure 7:
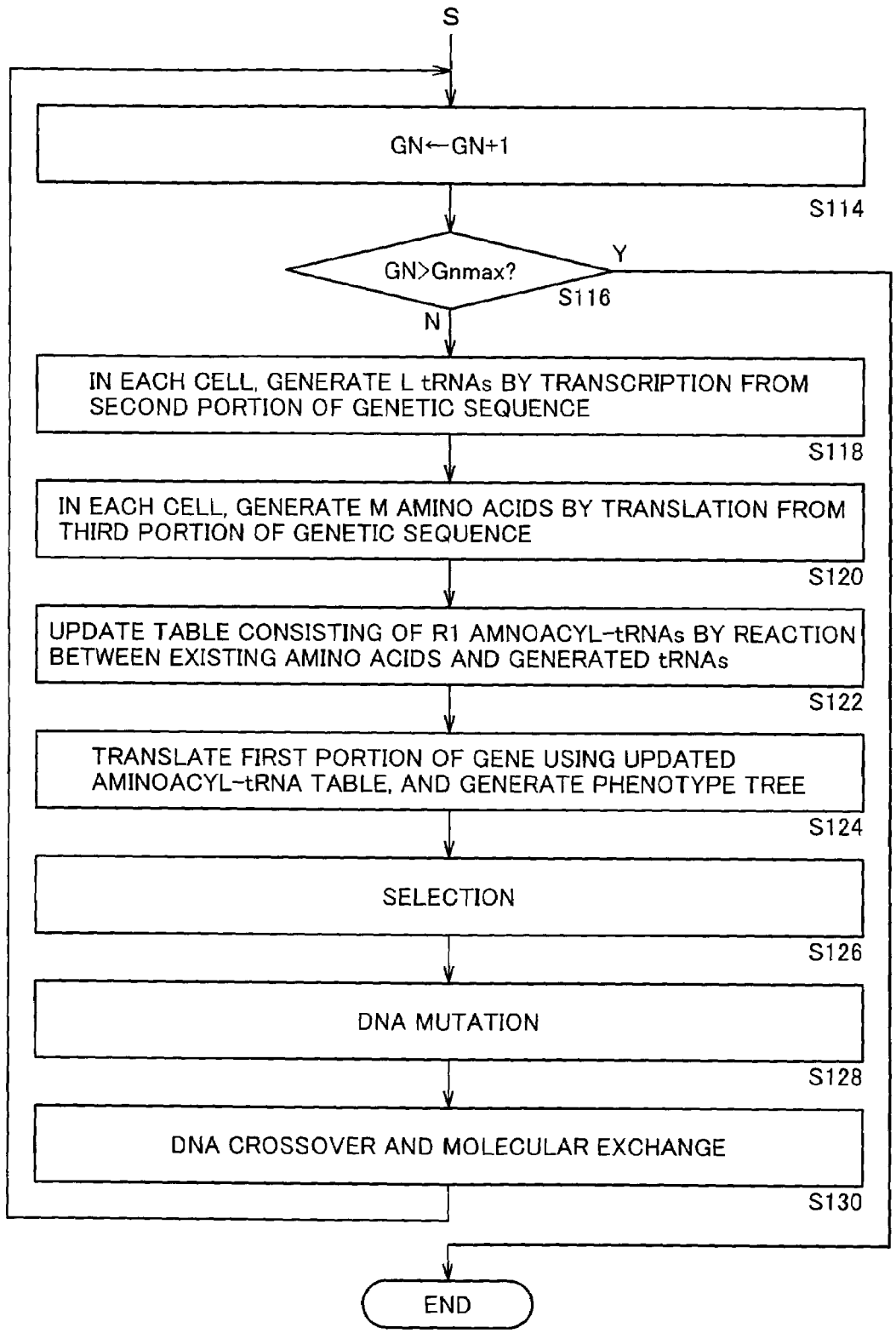
FIG. 7 is a second flow chart representing the flow of chemical genetic programming.

FIGS. 6 and 7 are flow charts representing the process flow of the chemical genetic programming.

First, referring to FIG. 6, when the process starts, initialization takes place (step S100).

In the initialization step, a storage area for variables and tables representing cells with metabolic mechanism is prepared for each of N cells, in the storage apparatus such as hard disk 124.

First, it is assumed that random rule numbers are allotted to the first and third portions of DNA, random rule numbers and random non-terminal symbols among prescribed symbols are allotted as pairs to the second portion of DNA, and the tRNA tables and aminoacyl-tRNAs are empty. A variable GN representing generation number is set to 1. $M_1$ amino acids are prepared for each cell.

FIG. 8 shows an example of initially prepared amino acids.

In the example shown in FIG. 8, the initial set includes 6 non-terminal symbols "I, N, O, R, Z, D" and 16 terminal symbols "x, ^, +, −, *, /, 0, 1, 2, 3, 4, 5, 6, 7, 8, 9" and amino acids represent mapping among these symbols for rewriting. All translations begin with the symbol "I" and end when all non-terminal symbols have been replaced by terminal symbols. Specifically, translations (rewriting) are continually applied to the non-terminal symbols in the current expression, in the left-to-right order in which they appear in the DNA, until all non-terminal symbols have been replaced. A non-terminal symbol is any symbol that can be further translated.

Further, mapping such as "N→(NON)" means that one symbol "N" branches to three symbols "N", "O" and "N". The amino acid library shown in FIG. 8 is only a demonstrative example, and it may contain larger number of symbols and other maps, and there may be a plurality of symbols from which translation starts.

Here, it is assumed that the symbols randomly allotted to the second portion of DNA correspond to the non-terminal symbols of the initial amino acid library. Further, it is assumed that random rule numbers of the first and third portions are allotted within the scope of the rule numbers of the second portion.

Again referring to FIG. 6, thereafter, in each cell, $L_1$ tRNAs are generated by transcription from the second portion of DNA (step S102).

When a randomly selected tRNA symbol matches a start symbol of randomly selected amino acid, these two are coupled to form one aminoacyl-tRNA, and by repeating this operation, a table containing $R_1$ aminoacyl-tRNAs is prepared (step S104).

Next, using the thus prepared aminoacyl-tRNA table, the first portion of the gene is translated, to create a phenotype tree (step S106).

Figure 9:
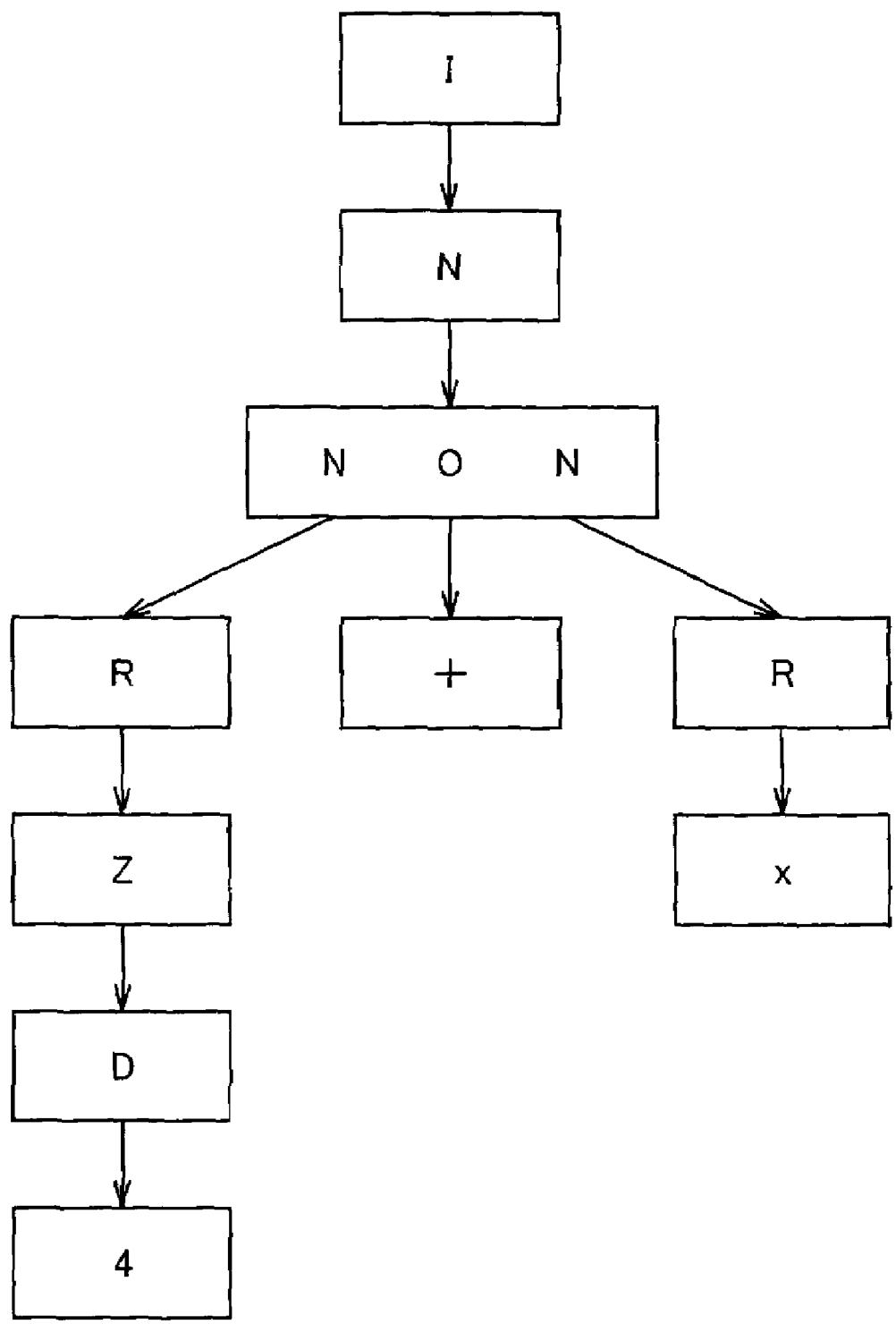
FIG. 9 shows an example of a generated phenotype tree.

FIG. 9 shows an example of the phenotype tree created in this manner.

In the example shown in FIG. 9, translation (rewriting) starts from the initial symbol "I", branched into three, the branches are respectively translated (rewritten) to terminal symbols "4", "+" and "x", and the translation process ends. Here, by this phenotype tree, a function (phenotype entity) of "4+x" is generated. In general, such final form may be a multi-variable function.

Again referring to FIG. 6, based on the comparison of the function generated by the phenotype tree with the target function, cell selection is performed (step S108).

Specifically, comparing the function represented by the phenotype tree against the target function, matching score (fitness) is computed. By way of example, in a prescribed domain of a variable, differences between values of the function represented by the phenotype tree and values of target function at a plurality of prescribed sample points are calculated, and the sum of the differences is squared. A function that monotonously decreases with respect to the square value is defined as an evaluation function, of which value is used as a matching score. The lower the degree of matching, the lower the matching score.

Then, cells are selected in accordance with a rule of selection that selects at a probability reflecting the matching score, such as wheel selection. Thus, the population of cells of the next generation is the set of such selection.

Then, DNA mutation is performed (step S110). Once cells have been selected into a next generation, each of the rule numbers of DNA in each cell is replaced by another valid code randomly with probability $p_m$.

Thereafter, DNA crossover and molecular exchange are performed (step S112).

After mutation, where there are N selected cells, all the cells are mated to make N/2 pairs. Each pair is subjected to a crossover operation with probability $p_c$. Namely, single point crossover is performed between randomly selected DNA pairs with probability $p_c$.

Further, each pair is subjected to molecular exchange. By way of example, 50% of each of tRNAs, amino acids and aminoacyl-tRNAs are randomly selected and exchanged in this molecular exchange operation.

Through such process of evolution, fit amino acids will be propagated through generations, while unfit amino acids will be eliminated. The complexity of amino acids and aminoacyl-tRNAs will grow in time, and productive combinations of amino acids can be merged into a single aminoacyl-tRNA table.

Then, the value of generation variable GN is incremented by one (step S114).

Thereafter, whether the generation variable GN is larger than a prescribed maximum generation number Gnmax or not is determined (step S116). If the generation variable GN is larger than the prescribed maximum generation number Gnmax, the process ends. If the generation variable GN is not larger than the prescribed maximum generation number Gnmax, the flow proceeds to step S118.

Thereafter, from L rule number-symbol pairs of the second portion of DNA, L tRNAs are created by transcription and added to the group of tRNA table (step S118). When the number of tRNAs exceeds $L_1$, tRNAs are randomly chosen and eliminated.

Then, M amino acids are created by translation from M rule numbers of the third portion of DNA (step S120). Translation is performed using an existing group of aminoacyl-tRNAs (aminoacyl-tRNA table), and aminoacyl-tRNAs of which rule numbers match the rule numbers on the DNA are selected at random. Amino acids having these aminoacyl-tRNAs are added to the group of amino acids (amino acid table).

Here again, when the number of amino acids exceeds $M_1$, some amino acids are randomly chosen and eliminated.

Then, the aminoacyl-tRNA table is updated by molecular reaction between tRNAs and amino acids (step S122). Specifically, when a randomly selected tRNA symbol matches a start symbol of a randomly selected amino acid, these two are coupled to create one aminoacyl-tRNA. This operation is repeated, and when $R_2$ new aminoacyl-tRNAs have been added to the aminoacyl-tRNA group, some aminoacyl-tRNAs are randomly chosen and eliminated, so that the number of aminoacyl-tRNAs does not exceed $R_1$. Consequently, it follows that one same rule number may have different mappings (amino acids) for rewriting.

Next, from the rule number of the first portion of DNA, a phenotype tree is created by translation using aminoacyl-tRNAs (step S124).

Thereafter, in the similar manner as in steps S108, S110, and S112, cell selection (step S126), DNA mutation (step S128) and DNA crossover and molecular exchange (step S130) operations are performed, and the flow returns to step S114.

(Experimental Results)

To verify the effectiveness of chemical genetic programming, a process to obtain mathematical function of a single variable through this procedure was performed.

The target function was $$f(x)=2x^6+3x^4+4x^2+100$$

over the domain (−5, 5). Matching score (fitness value) of each individual is defined as $$\text{fitness:} f=\exp(6\times\exp(-d/25000000)) \quad \text{(equation 1)}$$

where d is the sum of the differences between the generated function values and target function values squared at a finite set of points over a prescribed interval in the domain. The parameter values for these experiments are as follows.

The mutation probability, $p_m$, was 0.007, and crossover probability $p_c$ was 0.7.

The population size was 143.

Figure 10:
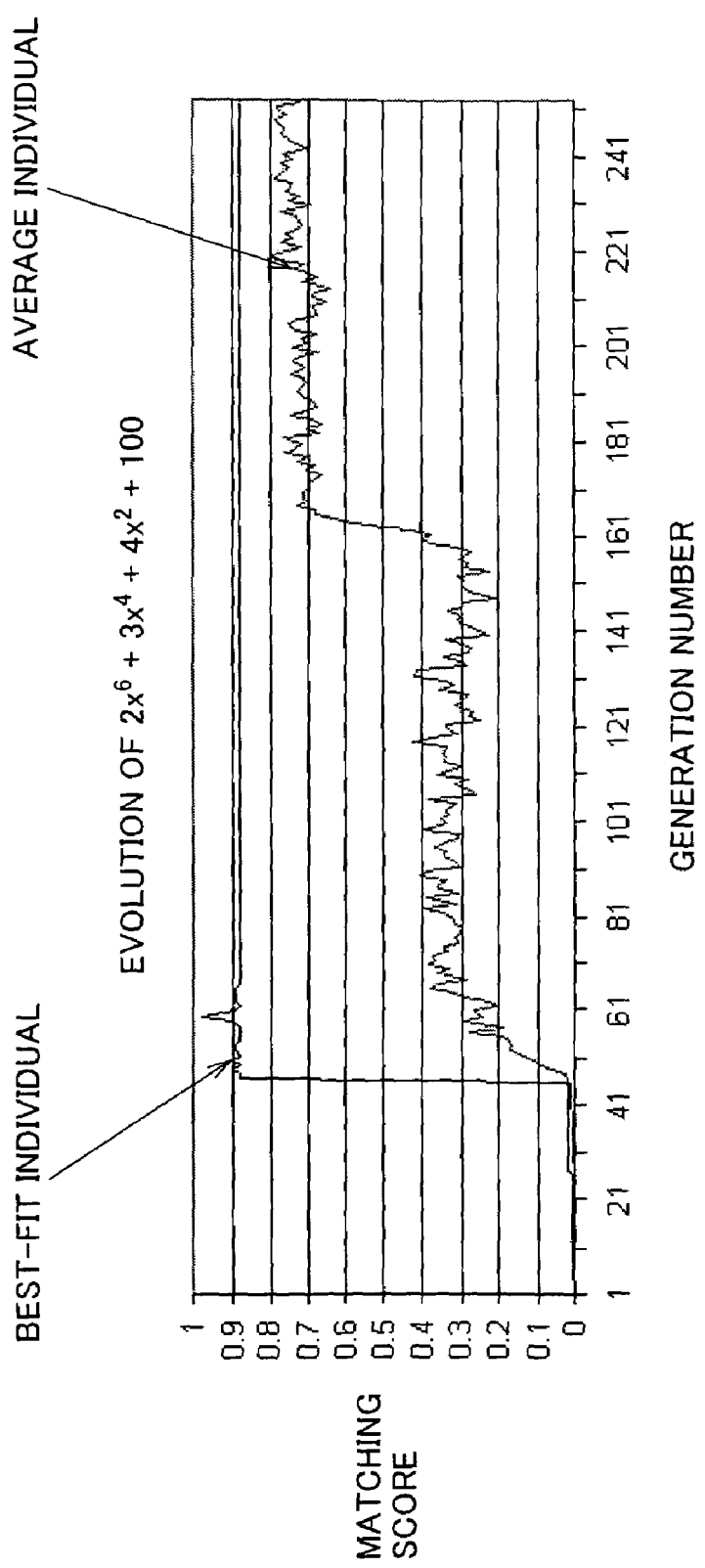
FIG. 10 is a graph showing generation-to-generation variation in fitness of best and average individuals.

FIG. 10 represents the best and average fitness values over the generations.

It can be seen that under these conditions, the best individual appears in generation 58.

Figure 11:
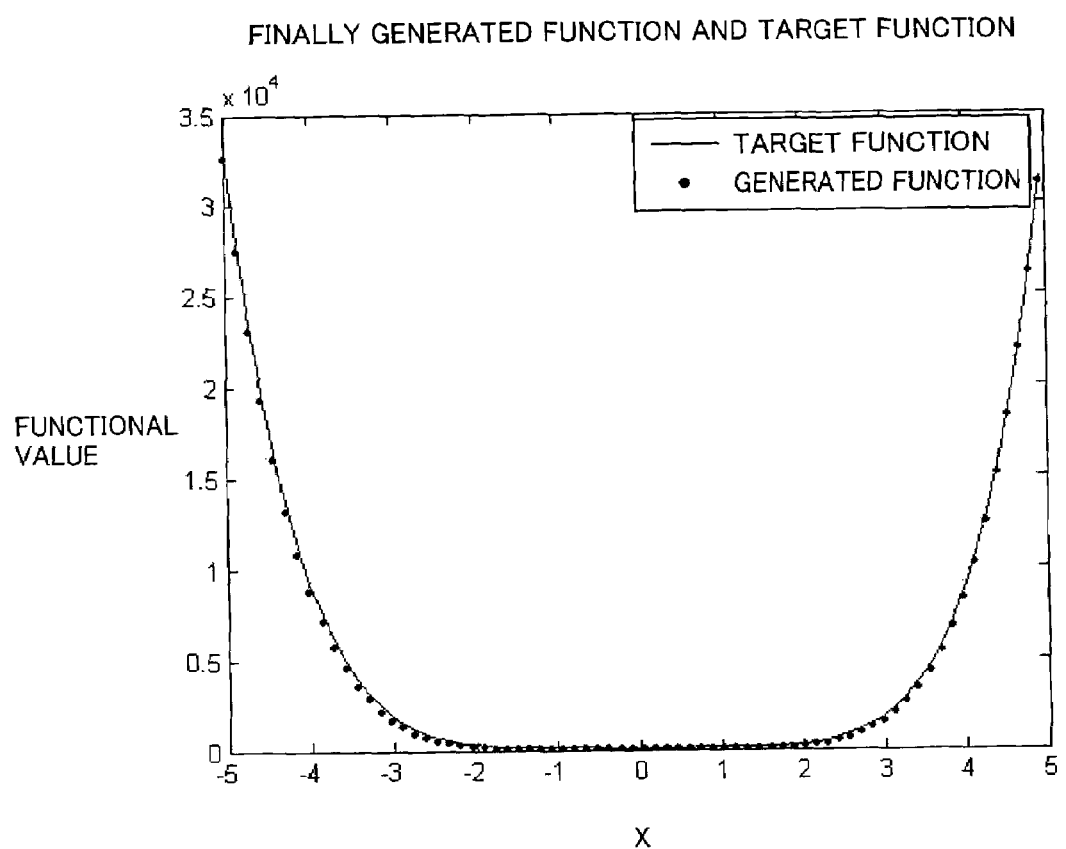
FIG. 11 shows a result of comparison between a finally obtained function and a target function.
Figure 12:
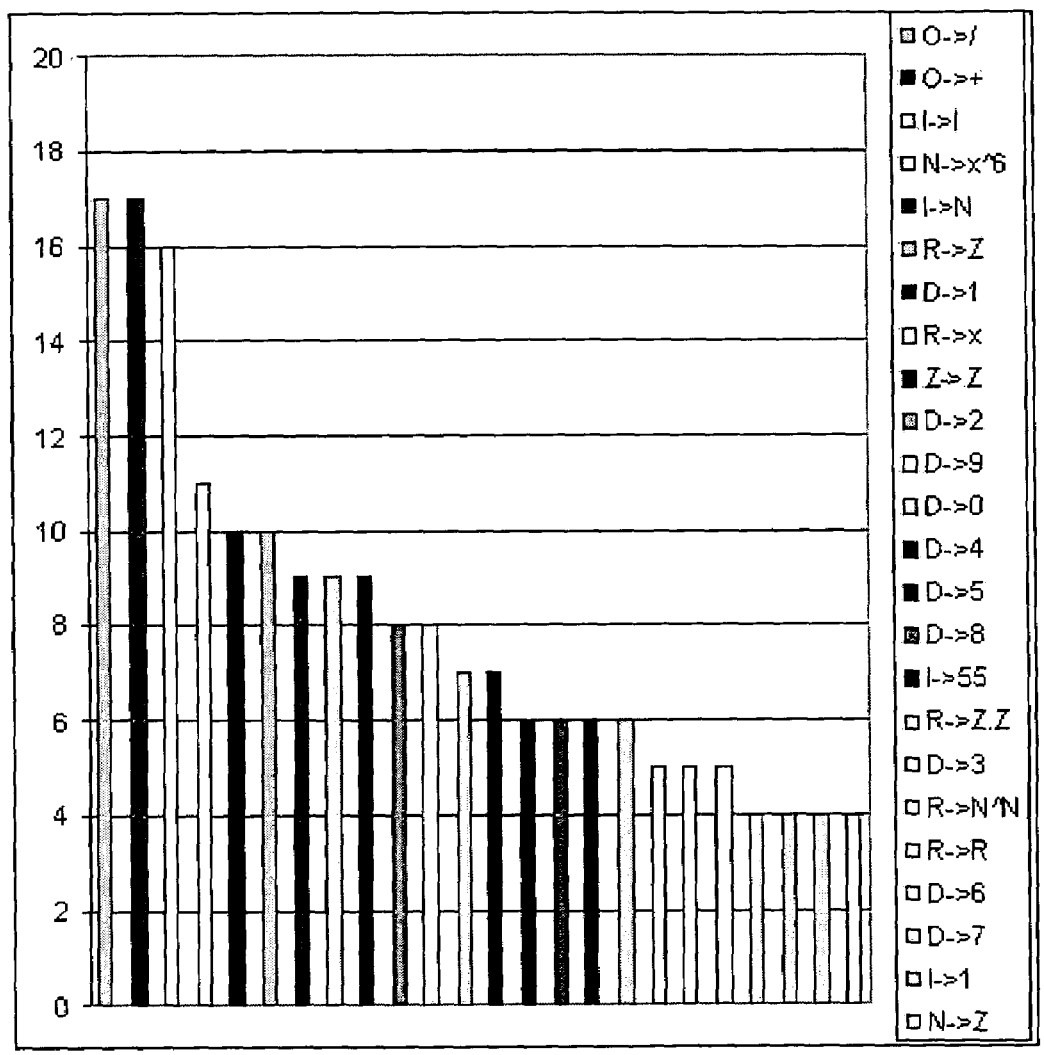
FIG. 12 is a histogram of amino acids evolved in cells.

FIG. 11 represents the result of comparison between the finally obtained function and the target function. FIG. 12 is a histogram of amino acids evolved in the cells.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A chemical genetic programming apparatus, comprising: a storing unit for storing individual information data of each individual, each of said individual information data including genetic information, transfer information, rewriting information, and a translation table, said transfer information including a plurality of rule number-symbol pairs, said rewriting information including mapping for rewriting said symbols, and said translation table being obtained by combining said transfer information and said rewriting information;

wherein said genetic information includes:

a first information including a sequence of said rule numbers for generating a phenotype entity, a second information for generating said transfer information, and a third information including a sequence of said rule numbers for generating said rewriting information;

said apparatus further comprising:

a transcribing unit for generating said transfer information by transcription from said second information;

a first translating unit for generating said rewriting information by translation based on said third information and said translation table;

an updating unit for updating said translation table by combining said rewriting information and said transfer information;

a phenotype entity generating unit for generating said phenotype entity by translation based on said first information and said translation table;

a selecting unit for selecting said individuals in accordance with fitness of a result represented by said phenotype entity with respect to a prescribed target and limiting population of said individuals stored in said storing unit to the number of said selected individuals;

a mutating unit for performing mutation on said genetic information;

a crossover processing unit for performing crossover process on said genetic information, said transfer information and said rewriting information; and an exchanging unit for exchanging among said individuals, said transfer information, said rewriting information, and information included in said translation table, whereby said selecting unit obtains a plurality of individuals corresponding to a desired phenotype entity after repeating operations.

2. The chemical genetic programming apparatus according to claim 1, wherein said symbol includes a terminal symbol forming the result represented by said phenotype entity and indicating an end of translation, and a non-terminal symbol indicating possibility of continuous translation; and said rewriting information includes continuous rewriting information from one of said non-terminal symbols to at least another one of said non-terminal symbols, and terminal rewriting information from one of said non-terminal symbols to one of said terminal symbols.

* * * * *